(12) United States Patent
Hamad

(10) Patent No.: US 6,732,057 B2
(45) Date of Patent: May 4, 2004

(54) METHODS FOR ENGINEERING AND MANUFACTURING SCORE-LINE-CRACK-RESISTANT LINERBOARD

(75) Inventor: Wadood Hamad, Mahwah, NJ (US)

(73) Assignee: International Paper Company, Stamford, CT (US)

( * ) Notice: Subject to any disclaimer, the term of this patent is extended or adjusted under 35 U.S.C. 154(b) by 504 days.

(21) Appl. No.: 09/891,986

(22) Filed: Jun. 26, 2001

(65) Prior Publication Data

US 2003/0065417 A1 Apr. 3, 2003

Related U.S. Application Data

(63) Continuation-in-part of application No. 09/855,325, filed on May 15, 2001, now Pat. No. 6,684,167.

(51) Int. Cl.[7] .................. G06F 19/00; G05D 31/12; G05D 17/00
(52) U.S. Cl. .................. 702/42; 702/35; 700/102; 700/295; 700/291
(58) Field of Search .................. 702/35, 39, 42, 702/191; 162/358.3, 361; 73/812, 849; 700/122, 109, 291, 295

(56) References Cited

U.S. PATENT DOCUMENTS

| | | |
|---|---|---|
| 1,612,415 A | 12/1926 | Carlson |
| 1,951,908 A | 3/1934 | Hayford .................. 73/51 |
| 2,462,826 A | 2/1949 | Waard et al. .................. 73/100 |
| 2,473,841 A | 6/1949 | Anderson .................. 73/100 |
| 4,958,522 A | 9/1990 | McKinlay .................. 73/847 |
| 5,199,305 A | 4/1993 | Smith et al. .................. 73/851 |
| 5,419,202 A | 5/1995 | Howard et al. .................. 73/849 |
| 5,566,570 A | 10/1996 | Hankel et al. .................. 73/159 |
| 5,574,227 A | 11/1996 | Allan .................. 73/849 |
| 5,606,134 A | 2/1997 | Stieber .................. 73/849 |
| 5,737,238 A | 4/1998 | Mouradian et al. .................. 364/507 |
| 6,050,149 A | 4/2000 | Yoshizawa .................. 73/849 |
| 6,158,287 A | 12/2000 | Satake et al. .................. 73/835 |

OTHER PUBLICATIONS

M. Ferahi, T. Uesaka and D. Lord; Finite Element Analysis of Scoring–Cracking in Corrugated Board, 1998 Progress in Paper Physics: A Seminar, Aug. 1998.

W.J. Whitsitt and R.C. McKee; An Investigation of Linerboard Cracking, Int. of Paper Chemistry, Appleton, Wisconsin, Dec. 1966.

*Primary Examiner*—Kamini Shah
(74) *Attorney, Agent, or Firm*—Ostrager Chong & Flaherty LLP

(57) ABSTRACT

A method of engineering score-line-crack-resistant multi-ply linerboard. The propensity for score-line cracking may be eliminated by engineering a ductile, plastically deforming top ply of a two-ply construction. Plasticity essentially extends the life span through which a material may deform (under external monotonic loading) prior to the initiation of damage (e.g., crack propagation) and ultimate failure. Hence the board's propensity for cracking is intrinsically linked to its fracture energy, or the energy consumed during plastic deformation (prior to failure). A top-ply fracture tester is used to measure the plastic energy consumed in deforming a single ply in a multi-ply system. The energy consumed in the plastic zone has shown excellent correlation to score-line cracking field performance of white-top linerboard. Machine trials were conducted to identify the principal variables that affect the propensity for score-line cracking. The principal variables identified were: fiber furnish (virgin vs. recycled), top-ply coverage (i.e., weight % of the top ply), refining energy of the top-ply furnish, and the starch and filler contents. Pulp quality, especially pulp viscosity, was also shown to play an important role in influencing cracking resistance. The engineering method provides recommendations for key operational parameters to produce score-line-crack-resistant white-top liner-board.

21 Claims, 13 Drawing Sheets

METHODS FOR ENGINEERING AND MANUFACTURING SCORE-LINE-CRACK-RESISTANT LINERBOARD

RELATED PATENT APPLICATION

This application is a continuation-in-part application claiming priority from U.S. patent application Ser. No. 09/855,325 filed on May 15, 2001 now U.S. Pat. No. 6,684,167.

FIELD OF THE INVENTION

This invention generally relates to the manufacture of paperboard products. In particular, the invention relates to multi-ply paperboard products having low score-line cracking propensity.

BACKGROUND OF THE INVENTION

There have been available few tests for evaluating score-line cracking, for instance, the score cracking angle test disclosed by Whitsitt and McKee in "Investigation of Improved Device for Evaluating the Cracking Potential of Linerboard," Institute of Paper Chemistry Summary Report, Project No. 1108-29 (1996). This test, first developed at the Institute of Paper Chemistry, fails to either measure a fundamental material property, or detect damage in a single ply. No meaningful correlations have thus been found over the years to score-line cracking performance in the field.

A recent test, disclosed by J. Gonzalez in "Score Cracking in Linerboard," M.S. Dissertation (No. 6190-Research), Institute of Paper Science and Technology, Georgia (2000), is not so much a predictive test, but rather is a set-up that attempts to replicate, rather poorly, scoring. It does not scientifically measure any board property that may prove to correlate to score-line cracking propensity in the field. The test comprises two motor-driven horizontal metal wheels forming essentially a nip compression. A linerboard sample (25 cm×12 cm), manually folded in half and fed between the flat metal wheels, undergoes a nip-type compressive force. The cracking percent of the folded sample is then measured visually or using a microscope.

The addition of starch to linerboard contributes to embrittling the board, hence reducing its ability to deform plastically, thereby speeding up catastrophic failure. Machine trials and previous experimental work conducted by the inventors confirmed the embrittling nature of (increasing) starch content in linerboard.

Experimental work has provided insight into the root causes of the propensity for score-line cracking in white-top linerboard (especially 69 lb.). [The designation "white-top" refers herein to linerboard products which contain more than one layer of fibers with the top layer being composed of recycled or virgin bleached pulp.] The mechanistic basis for designing a score-line-crack-resistant two-ply linerboard is grounded in three (non-mutually exclusive) functional factors: (1) the ability of the top ply to undergo large plastic (irreversible) deformation prior to failure; (2) the ability of the base ply to compress elastically while the top ply is deforming (plastically); and (3) in order for (1) and (2) to simultaneously apply, the interlaminar (ply) bond must be low enough (but adequate to ensure against delamination) to allow the top ply to "slide" over the base ply. Achieving this requires a testing method capable of predicting plastic deformations, or the fracture toughness, of the top ply alone, and able to correlate such a measurement with score-line cracking propensity in the field.

In materials science and engineering, the term "material" has a precise meaning. It refers to either a pure substance or an alloy that can be approximated as essentially homogeneous in composition. When more than one substance or material are combined, and when this combination has internal structural heterogeneity, the term "composite material" is used. According to this definition, wood fibers may be regarded as composite materials, or, specifically, composite tubes of cellulosic microfibrils embedded in an amorphous matrix of hemicellulose and lignin. Structurally, paper or board is, however, a network. On a microscopic scale, paper or board is a cellulosic network of crossing fibers filled with voids; macroscopically, it could be regarded as a continuum with inherent (micro)cracks and flaws being "smeared out" for the purpose of analysis. For practical issues related, for instance, to box construction, such as scoring, it may be deemed appropriate that linerboard be dealt with as a continuum whose material properties and structural analysis are determined relying on theories of elasticity and plasticity from the field of solid mechanics. Thus, two-ply linerboard constructs comprise two elastic-plastic sheet-like materials whose properties may be analyzed orthotropically. Safeguarding against, for instance, cracking in the top ply during scoring would necessitate attention principally to: i) the extent of (plastic) deformability in each ply; and ii) inter-ply stresses.

Linear elastic materials load and unload along the same path; crack growth in such a material can be represented graphically by a load-displacement curve which is linear up to the point of crack propagation, and the displacement is zero when the specimen is unloaded. The energy consumed in the fracture process is therefore equivalent to the area enclosed under the curve. The irreversible work consumed during elastic fracture is confined to thin boundary layers along the faces of the propagating crack.

Paper and board, however, are tough, ductile materials (the extent of which depends on furnish composition and papermaking conditions) whose yield stress is low. When such a material is strained, it yields not only at the point(s) of crack initiation, but away from these points too. Thus, irreversible deformation is no longer confined to the thin boundary layer along the faces of the propagated crack (as in elastic fracture), but is spread throughout the material. In addition to the work required in the crack tip process zone, significant irreversible work is consumed in the yielded regions away from the crack. It is important to recognize that the plastic deformation outside the fracture process zone is not essential to the process of fracture. Consequences of the plastic flow include curvature in the load-displacement curve on loading, and displacement irreversibilities upon unloading, both in a specimen without a crack and a specimen with a crack.

The work done during loading, given by the area under the load-displacement curve, represents the combined contribution to fracture and remote flow. These two works are difficult to separate experimentally. However, a methodology has been developed to separate the elastic and plastic portions of the fracture energy consumed in deforming the top-ply of two-ply linerboard systems. This methodology has been designed so that the measured plastic contribution of the work done during the fracture process correlates well with predicting the propensity of linerboard to score-line cracking during converting operations.

More specifically, a top-ply fracture tester has been developed which comprises two clamps in which a sample is placed; one of the clamps is fixed, the other rotates the sample around a spindle. When bending the sample, it is under a net tensile force, which is recorded using a load cell. The testing set-up measures the fracture energy (and toughness) in a single ply of a multi-ply structure. The top-ply fracture tester induces fracture in the top ply only, and allows the identification of elastic and plastic regions in a single ply. Score-line cracking resistance essentially emanates from the ability of the sheet to deform plastically (in the top ply), and analysis has shown that it is (perfectly) correlated with the two components of the top-ply plastic zone: the work done, or energy consumed, during the crack-to-gap transition and during the gap-to-flap transition. This accurate measure formed the cornerstone for experimentation into examining the root cause(s) of score-line cracking, and paved the path for the ultimate design of crack-resistant linerboard.

SUMMARY OF THE INVENTION

The present invention is directed to a method for engineering a multi-ply paperboard system having enhanced resistance to score-line cracking. The research work conclusively indicated that the propensity for score-line cracking may be eliminated by engineering a ductile, plastically-deforming top ply of the multi-ply construction. Plasticity essentially extends the life span through which a material may deform (under external monotonic loading) prior to the initiation of damage (e.g., crack propagation) and ultimate failure. Hence the board's propensity for cracking is intrinsically linked to its fracture energy, or the energy consumed during plastic deformation (prior to failure).

In accordance with one preferred embodiment, the methodology of statistical design of experiments (DOE) is employed to engineer a score-line-crack-resistant white-top linerboard. A statistically designed experiment allows one to efficiently make empirical measurements at the limits of the parameter ranges, and with minimal number of experiments or "trials", derive a prediction equation of state which describes the process of manufacturing crack-resistant linerboard. First, a list of the principal factors in the manufacture of score-line-crack-resistant linerboard was derived based on experimental findings. In accordance with the preferred embodiment, the principal variables that have been identified to affect the propensity for score-line cracking are: fiber furnish (virgin vs. recycled), top-ply coverage (i.e., weight of the top ply), refining energy of the top-ply furnish, and the starch and filler contents. Pulp quality, especially pulp viscosity, was also shown to play an important role in influencing cracking resistance.

Selected input factors were varied in a statistically designed experiment. The response variables were then physically measured. In particular, a specially designed top-ply fracture tester was used to measure the plastic energy consumed in deforming a single ply in the multi-ply system. The energy consumed in the plastic zone can be characterized by two components related to the level of damage in the top ply, viz.: crack, the point of crack initiation; gap, the further propagation of the cracks; and flap, the consolidation of the cracks into rupture zones. The two components, energy consumed during the crack-to-gap transition and energy consumed during the gap-to-flap transition, have shown excellent correlations to score-line cracking field performance of white-top linerboard.

Following the measurement of the physical properties of interest, a statistical analysis of the response variables as a function of the input (DOE) variables was used to derive predictive equations of state. The result of these experimental studies was a set of proposed values for key operational parameters for the production of white-top linerboard having optimal score-line cracking resistance.

The invention is further directed to a method of manufacturing score-line-crack-resistant linerboard in which key operational values are optimized.

DETAILED DESCRIPTION OF THE PREFERRED EMBODIMENTS

Figure 1:
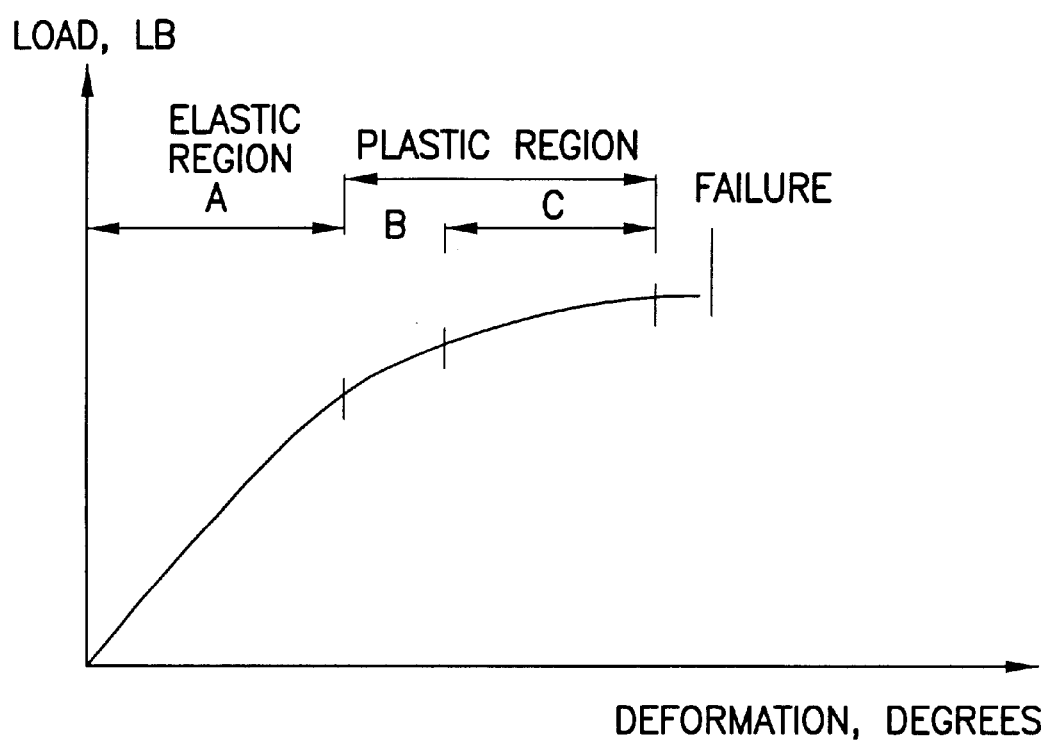
FIG. 1 is a schematic representation of load versus deformation to show the principles of fracture as applied to deforming the top ply in a two-ply linerboard construct: A) the elastic region until crack initiation; B) the crack-to-gap transition; C) the gap-to-flap transition; B+C) crack-to-flap transition.

Machine trials were conducted with the goal of engineering a ductile, plastically deforming top ply of a two-ply paperboard system. In accordance with the preferred embodiment of the invention, the two-ply board was a white-top linerboard. As background for disclosure of the present invention, the conventional procedure for manufacturing white-top linerboard will be generally described.

The first step in the manufacture of white-top linerboard is the refining of fibers, wherein individual fibers are fibrillated. Usually, softwood and hardwood fibers are refined together, although separate refiners could be used for virgin and recycle furnish. In the case of a two-stage refining system, the fibers are first refined in a primary refiner, where most of the energy is applied, and then are refined in a tickler refiner. Refining is done before the pulp goes to the paper-machine.

The papermaking process comprises three overall stages: wet end, forming section and dry end. The wet end includes the head boxes; the forming section includes the forming tables. The forming section is followed by pressing, drying, calendering and winding.

White-top linerboard is typically formed on a paper machine capable of producing multilayer product. One paper machine suitable for making a two-ply product is a conventional Fourdrinier machine fitted with two head boxes, one containing the furnish for the bottom ply and the other containing the furnish for the top ply. Each head box contains a pulp slurry which is usually over 99% water. Starch and other chemical additives are generally added in the head boxes. One headbox deposits the bottom ply on a forming table of the Fourdrinier machine. At a suitable position along the forming table, vacuum is applied using conventional suction boxes and then the second headbox adds a top ply to the bottom ply. Water is removed by foils and by a suction roll. The web, typically having a solids content of 20–22%, exits the Fourdrinier machine and enters a conventional press section (not shown), which removes additional water (typically to a solids content of 38–42%).

In the manufacture of white-top linerboard, the top layer furnish comprises bleached pulp, which can be either recycled or virgin or a combination thereof. The bottom layer furnish is unbleached pulp, which can be either recycled or virgin or a combination thereof. Conventionally, the top layer can be 5–80% of the total basis weight.

Following pressing, the two-ply web is dried in the main dryer section of the paper machine. It is common practice to then surface size the dried web at a size press (e.g., of the puddle or metering type) where the amount of pickup can be controlled. Sizing operations are carried out primarily to provide paper/paperboard with resistance to penetration by aqueous solutions. The treatment also improves the surface characteristics and certain physical properties of the paper/paperboard. During surface sizing, surface voids in the sheet are filled with starch or other binder particles. The size press can be any of the known types in the art. In the size press, the web passes through the nip between a pair of opposing size press rolls. The nip formed by the size press rolls is flooded with sizing solution supplied on both sides of the web by respective banks of solution supply tubes spaced in the sheet cross direction. The web absorbs some of the solution and the unabsorbed solution is removed by the pressure in the nip.

It is known to use the size press to add a variety of agents for a variety of purposes (e.g., starch and polyvinyl alcohol for strength, pigments such as calcium carbonate, clay for improving the brightness and smoothness of the product). The starch solution (e.g., unmodified, acid modified, pre-oxidized or hydroxyethylated) may have a starch concentration in the range of 1–10%. The sized press-treated paperboard is dried in the dryer section to a moisture level of 1–10%.

Following the size press treatment and drying, the web is passed through a calendering section. In a typical calendering operation, the top surface of the linerboard product is pressed against a heated surface to effect hot calendering. The top layer can optionally be moistened using moisturizing means before the paperboard enters the calendering nip to further enhance the smoothness or gloss consistent with the principle of moisture gradient calendering. The moisturizing showers may consist of water showers (e.g., hydraulic, air atomized or ultrasonic showers) or steam showers or combination of water showers and steam showers. The moisturizing showers can be used to correct for nonuniformity in moisture profile. If steam showers are used in conjunction with water showers, the preferred configuration would have the steam showers following the water showers. The location of the moisturizing showers will be such that the dwell time between moisturization and the heated nip location varies between 0.05 and 3 sec.

In accordance with one aspect of the present invention, a statistically designed experiment can be used to engineer score-line-crack-resistant white-top linerboard. The inventors ran three designed experiments: the first and second designed experiment were run during production of white-top linerboard having a basis weight of 42 lb (with 100% recycled furnish); and the third designed experiment was run during production of white-top linerboard having a basis weight of 69 lb (with 100% virgin fibers in the top ply). Significant trends were identified and successfully implemented in a subsequent 69-lb white-top production run. The exercise further resulted in proposing key operational parameters (KOPs) for the production of white-top linerboard (preferably with 100% virgin fibers in the top ply) with optimal score-line cracking resistance.

As part of the designed experiments, various material properties of multi-ply linerboard samples were measured. Using a top-ply fracture tester, samples of linerboard were bent and the energy consumed up to crack initiation, during the crack-to-gap transition and during the gap-to-flap transition were measured. The term "crack" refers to observable discontinuities in the outermost ply under observation; the term "gap" refers to the propagation of macro-cracks leading to their opening up; and the term "flap" refers to the increase in the gap, or crack opening, and ultimate delamination of the ply (under observation) upon further load application. The peel strength of samples was measured using the test designated ASTM D1876-95. The burst strength of samples was measured using the test designated TAPPI T807 OM-99. The ring crush strength (in the cross-direction, CD) was measured using the test designated TAPPI T818 CM-97.

The preferred top-ply fracture tester is of the type disclosed in U.S. patent application Ser. No. 09/855,325 filed on May 15, 2001. That top-ply fracture tester provides an accurate measure of the energy consumed in deforming the top ply of a multi-ply board system. This capability allows one to investigate score-line cracking phenomena occurring in the top ply of the linerboard. The top-ply fracture tester induces fracture in the top ply only, and allows the identification of elastic and plastic regions in a single ply, as shown in FIG. 1. In the graph shown in FIG. 1, region A is the elastic region up to crack initiation; region B is a plastic region encompassing the crack-to-gap transition; and region C is a plastic region encompassing the gap-to-flap transition.

The top-ply fracture tester is a computerized instrument that is programmed to report each of three values for each replicate and then give the average and standard deviation of each value after the last replicate is run. The reported values are the following: (1) The area under the stress-strain curve up to the point of crack initiation in the outermost ply. The area under the stress-strain curve represents the energy consumed, in this case up to crack initiation. (2) The area under the stress-strain curve from the crack to the gap. This area represents the energy consumed during the process following crack initiation and before the inception of gap formation, or crack opening. (3) The area under the curve from the gap to the flap. This area represents the energy consumed during the process of gap formation, or crack opening, and ultimate delamination within the same ply.

Figure 2:
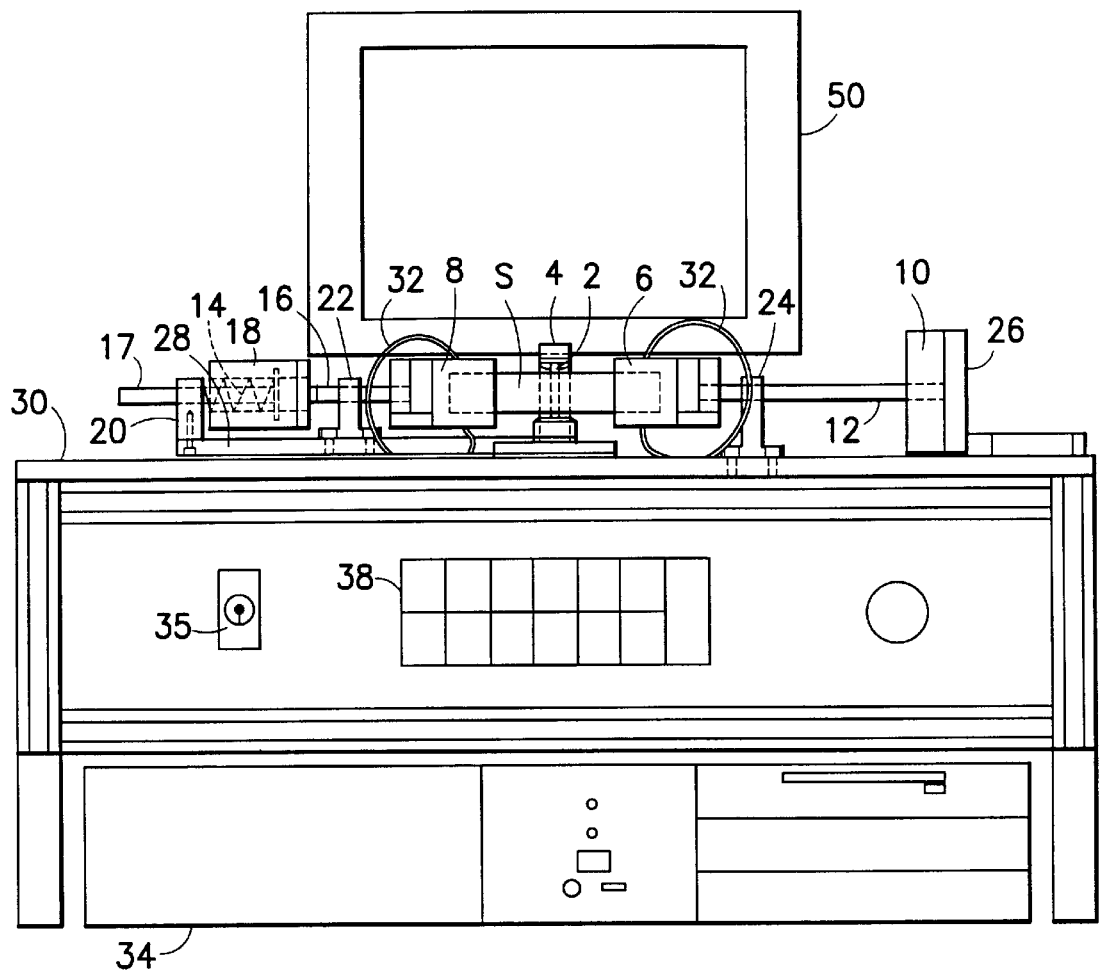
FIG. 2 is a schematic showing a front view of a top-ply fracture tester in accordance with the preferred embodiment of the invention.
Figure 3:
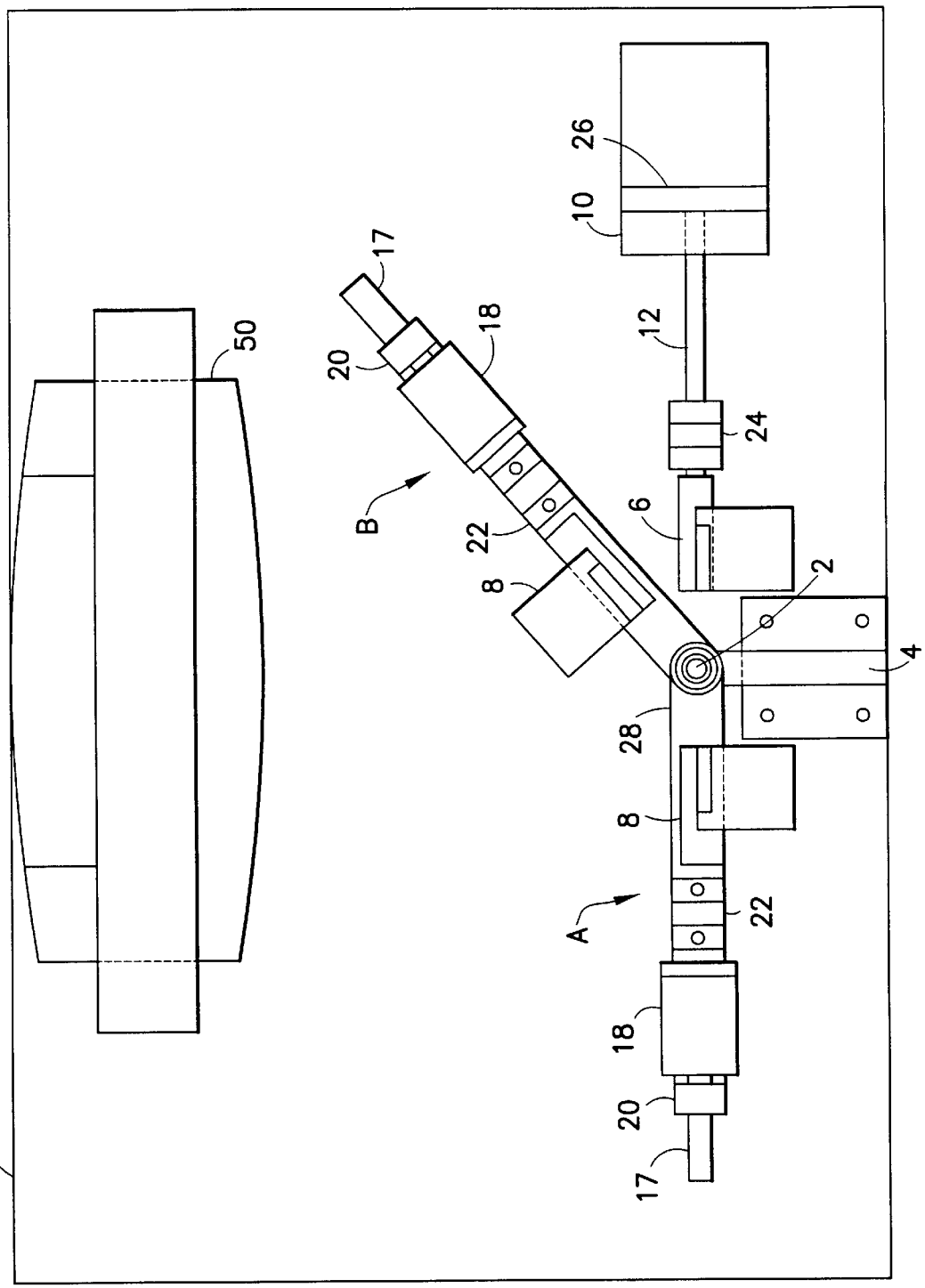
FIG. 3 is a schematic showing a top view of the top-ply fracture tester in accordance with the preferred embodiment of the invention. The rotating arm is shown in its initial and final positions.
Figure 4:
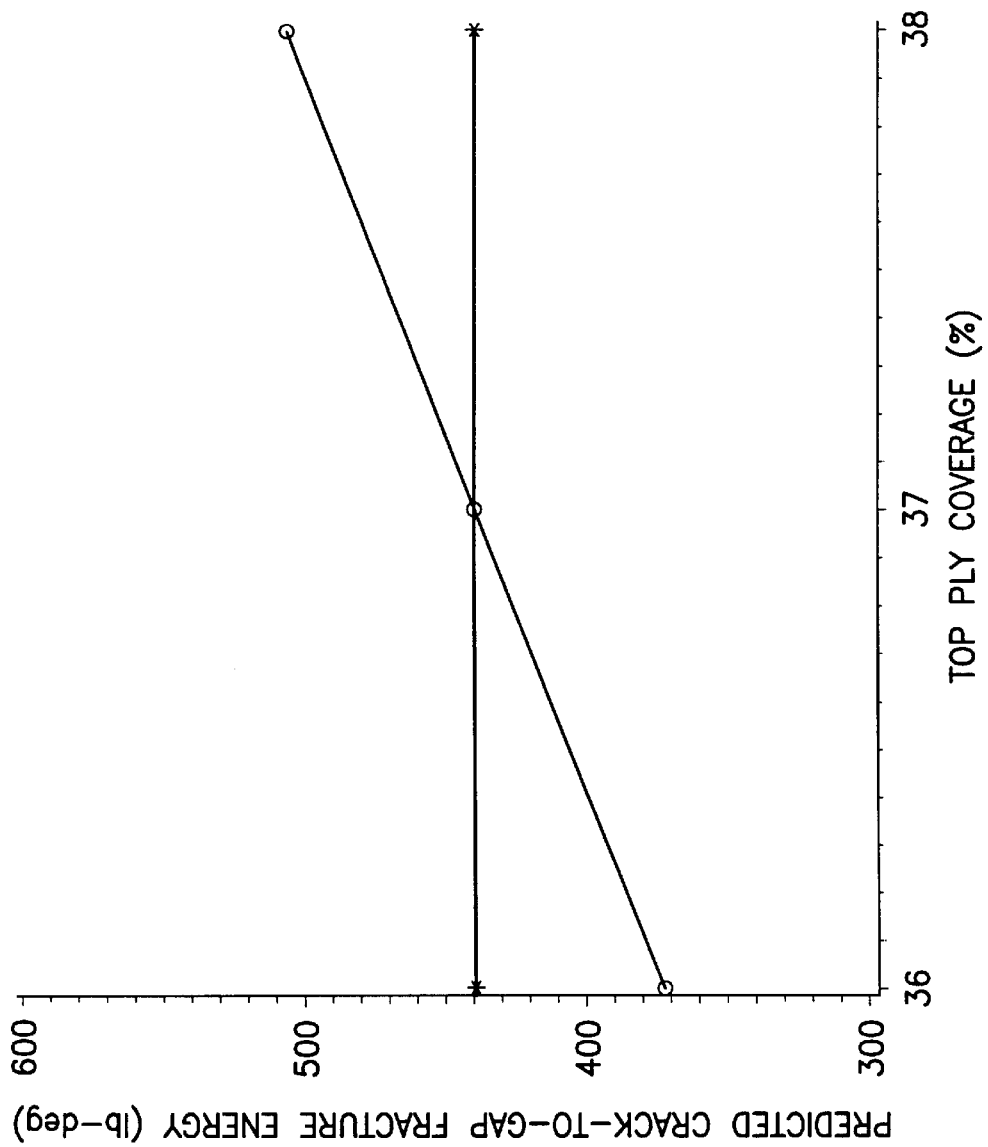
FIG. 4 is a graphical representation of how the predicted crack-to-gap fracture energy (lb*deg) varies with respect to top-ply coverage (wt. %) when the tickler refining level was 1,450 kW for two different wet end starch levels: (❈) 20 lb/ton; (*) 30 lb/ton.
Figure 5:
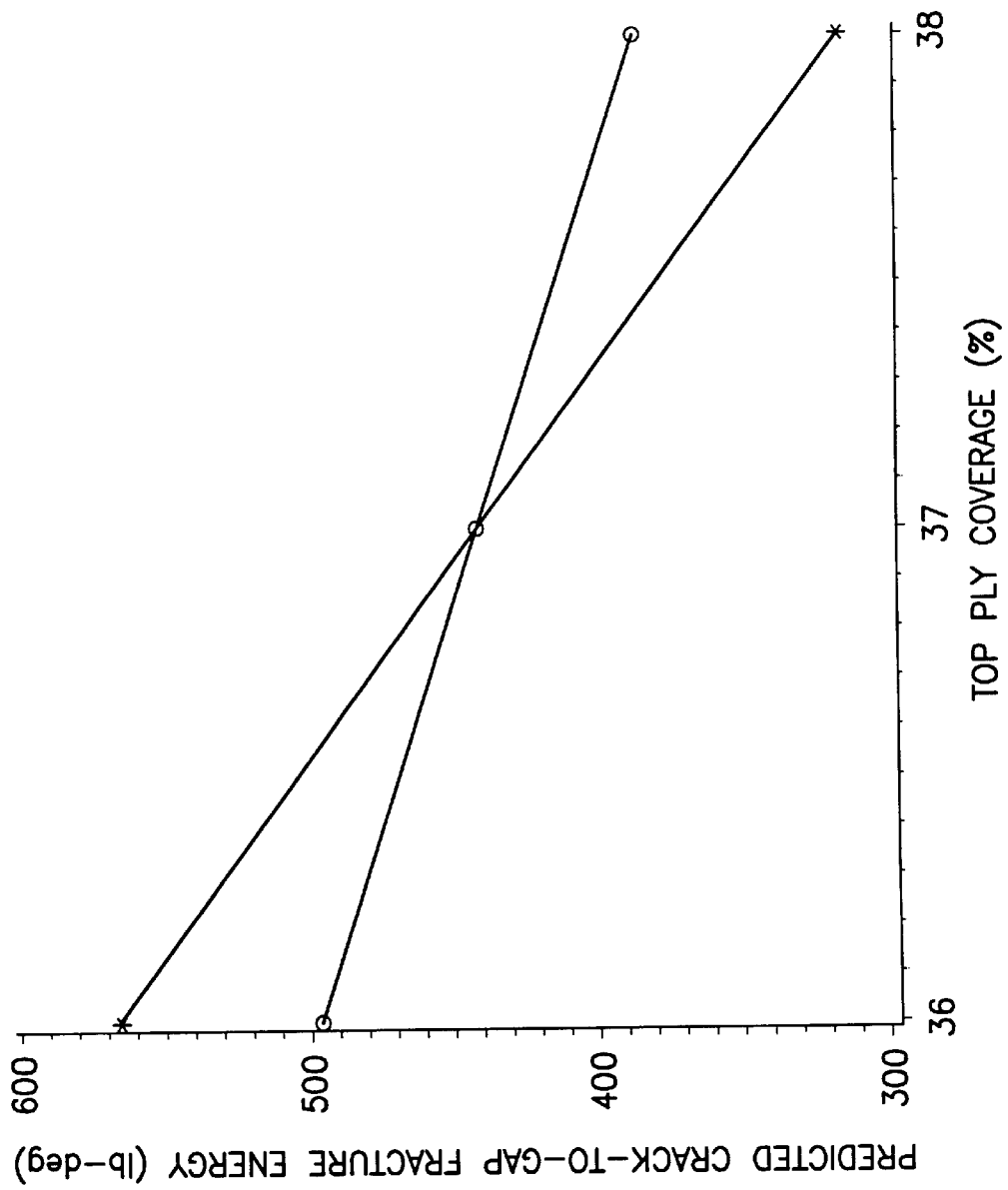
FIG. 5 is a graphical representation of how the predicted crack-to-gap fracture energy (lb*deg) varies with respect to top-ply coverage (wt. %) when the tickler refining level was 1,750 kW for two different wet end starch levels: (❈) 20 lb/ton; (*) 30 lb/ton.
Figure 6:
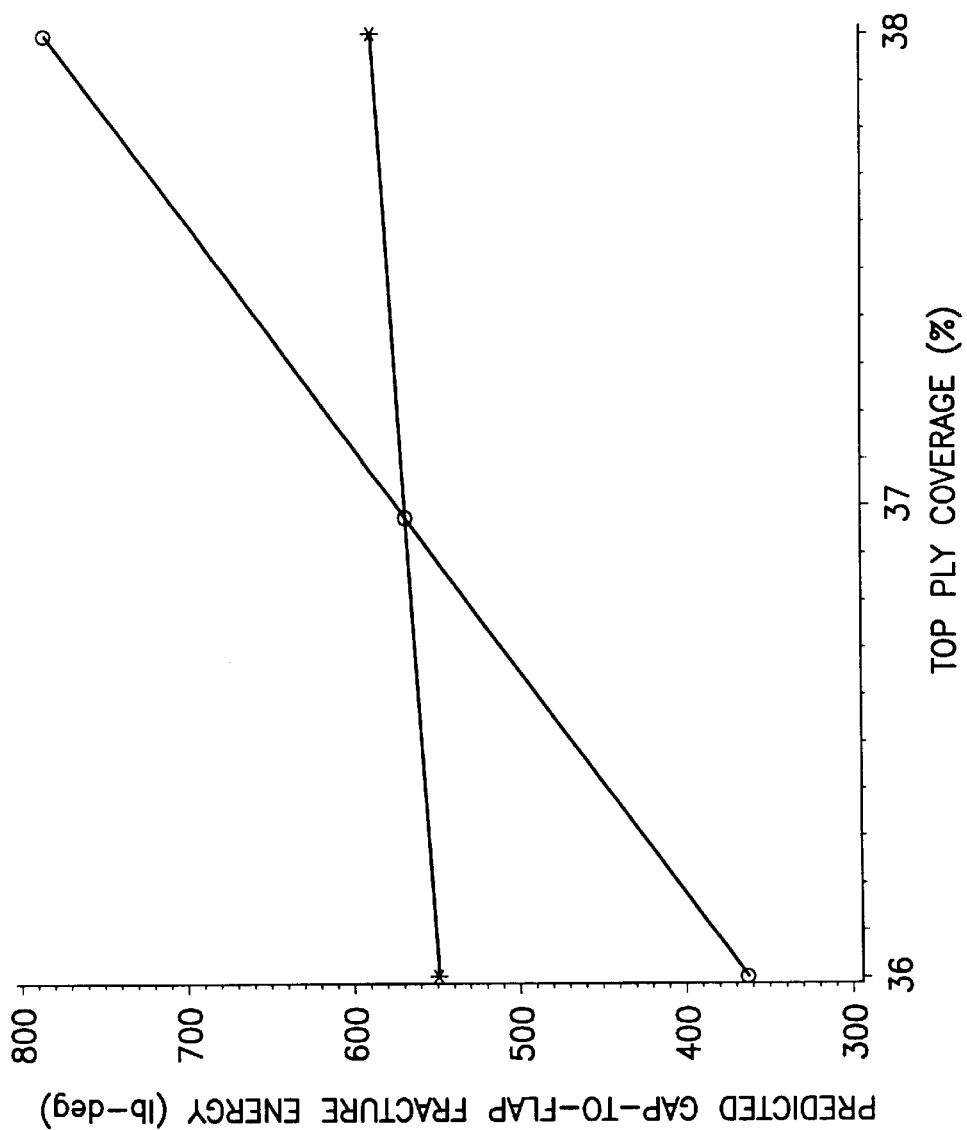
FIG. 6 is a graphical representation of how the predicted gap-to-flap fracture energy (lb*deg) varies with respect to top-ply coverage (wt. %) when the tickler refining level was 1,450 kW, for two different wet end starch levels: (❈) 20 lb/ton; (*) 30 lb/ton.
Figure 7:
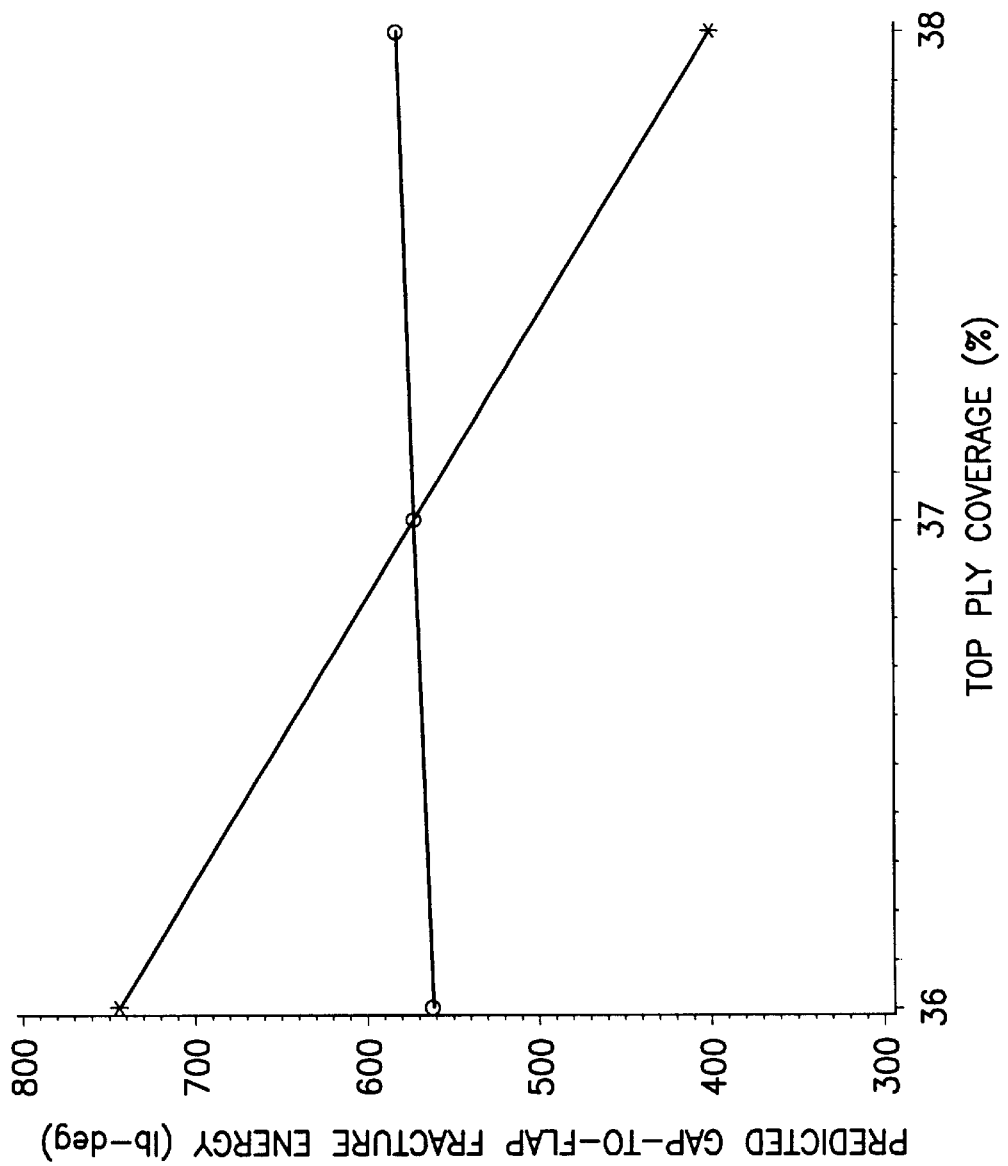
FIG. 7 is a graphical representation of how the predicted gap-to-flap fracture energy (lb*deg) varies with respect to top-ply coverage (wt. %) when the tickler refining level was 1,750 kW, for two different wet end starch levels: (❈) 20 lb/ton; (*) 30 lb/ton.
Figure 8:
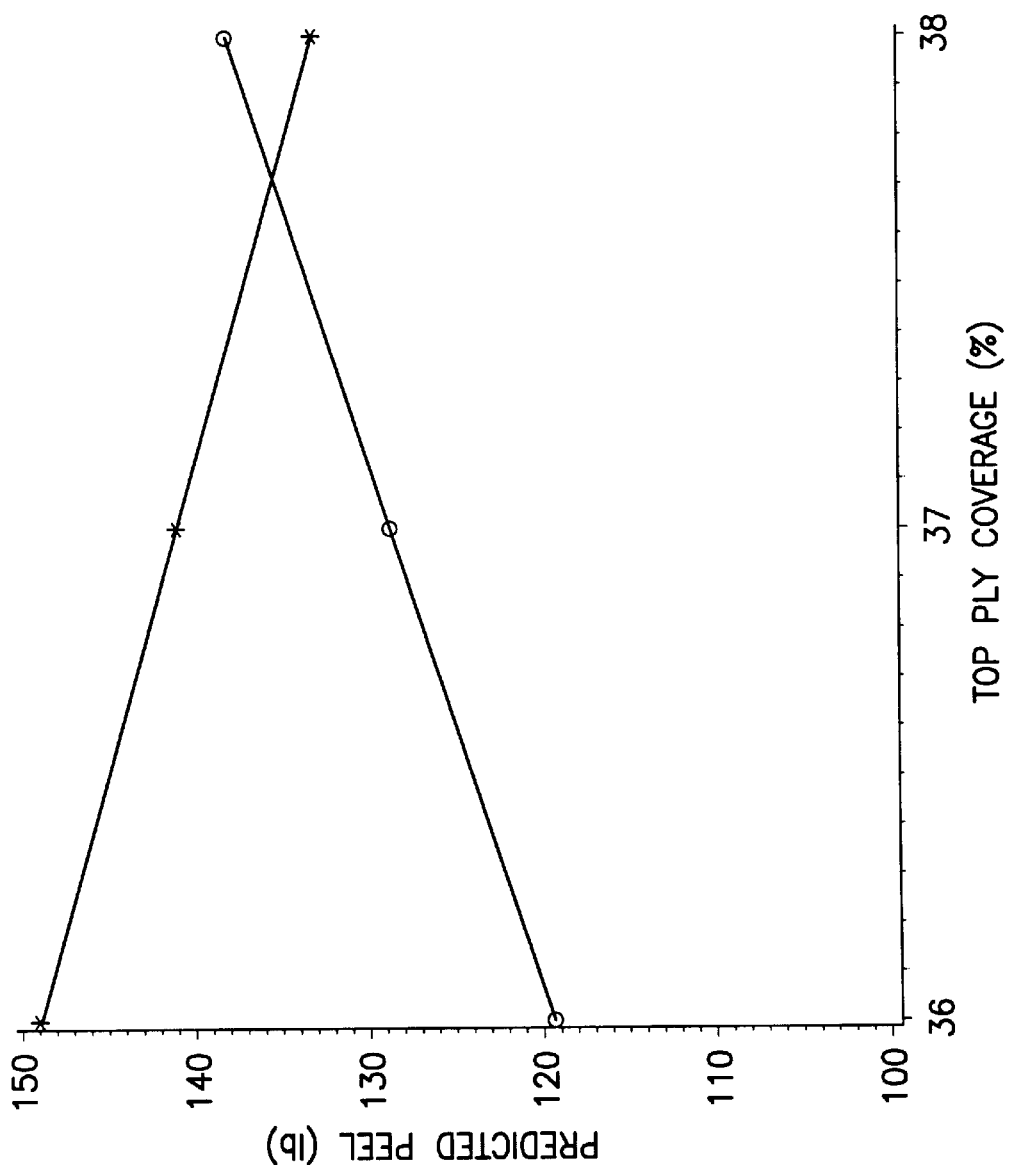
FIG. 8 is a graphical representation of how the predicted peel strength (lb) varies with respect to top-ply coverage (wt. %) when the tickler refining level was 1,450 kW, for two different wet end starch levels: (❈) 20 lb/ton; (*) 30 lb/ton.
Figure 9:
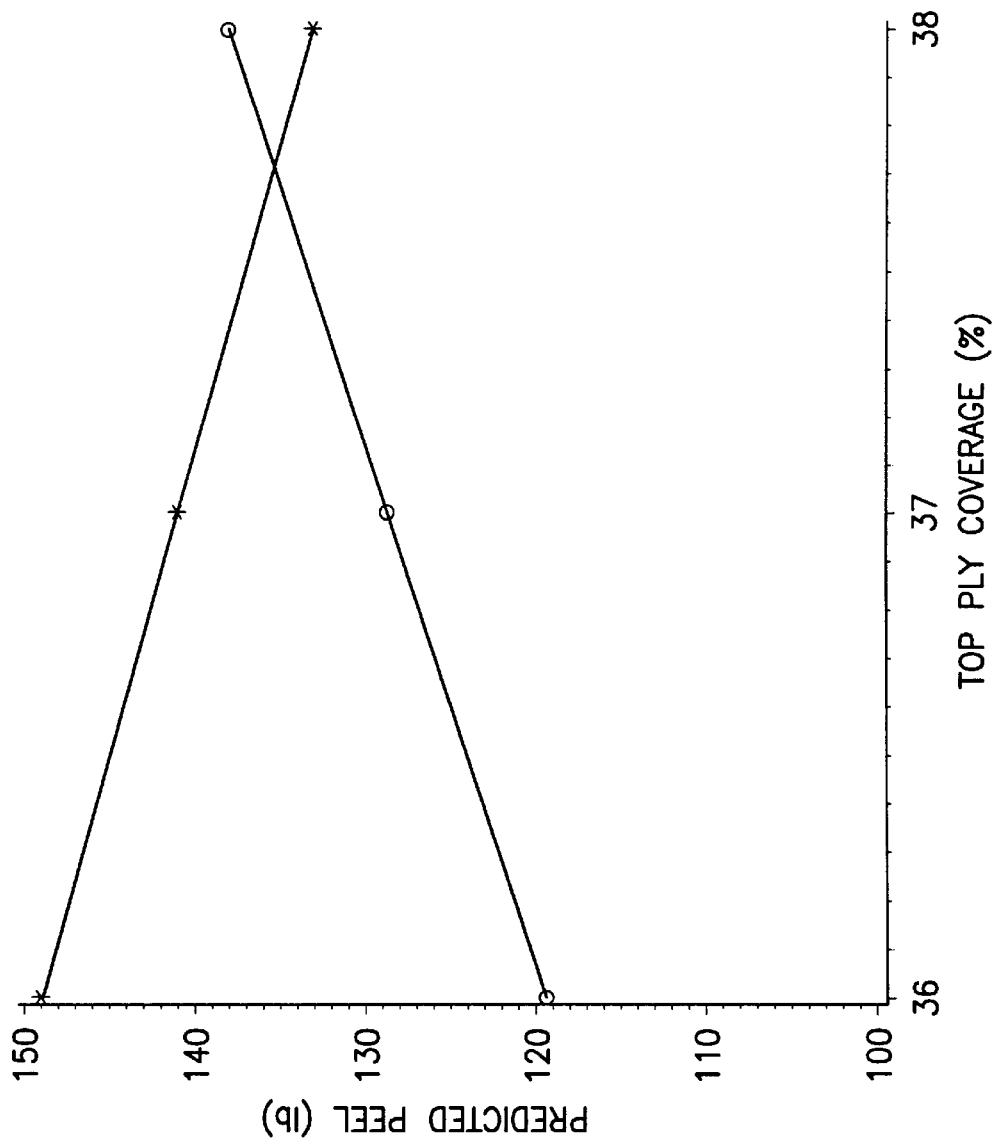
FIG. 9 is a graphical representation of how the predicted peel strength (lb) varies with respect to top-ply coverage (wt. %) when the tickler refining level was 1,750 kW, for two different wet end starch levels: (❈) 20 lb/ton; (*) 30 lb/ton.
Figure 10:
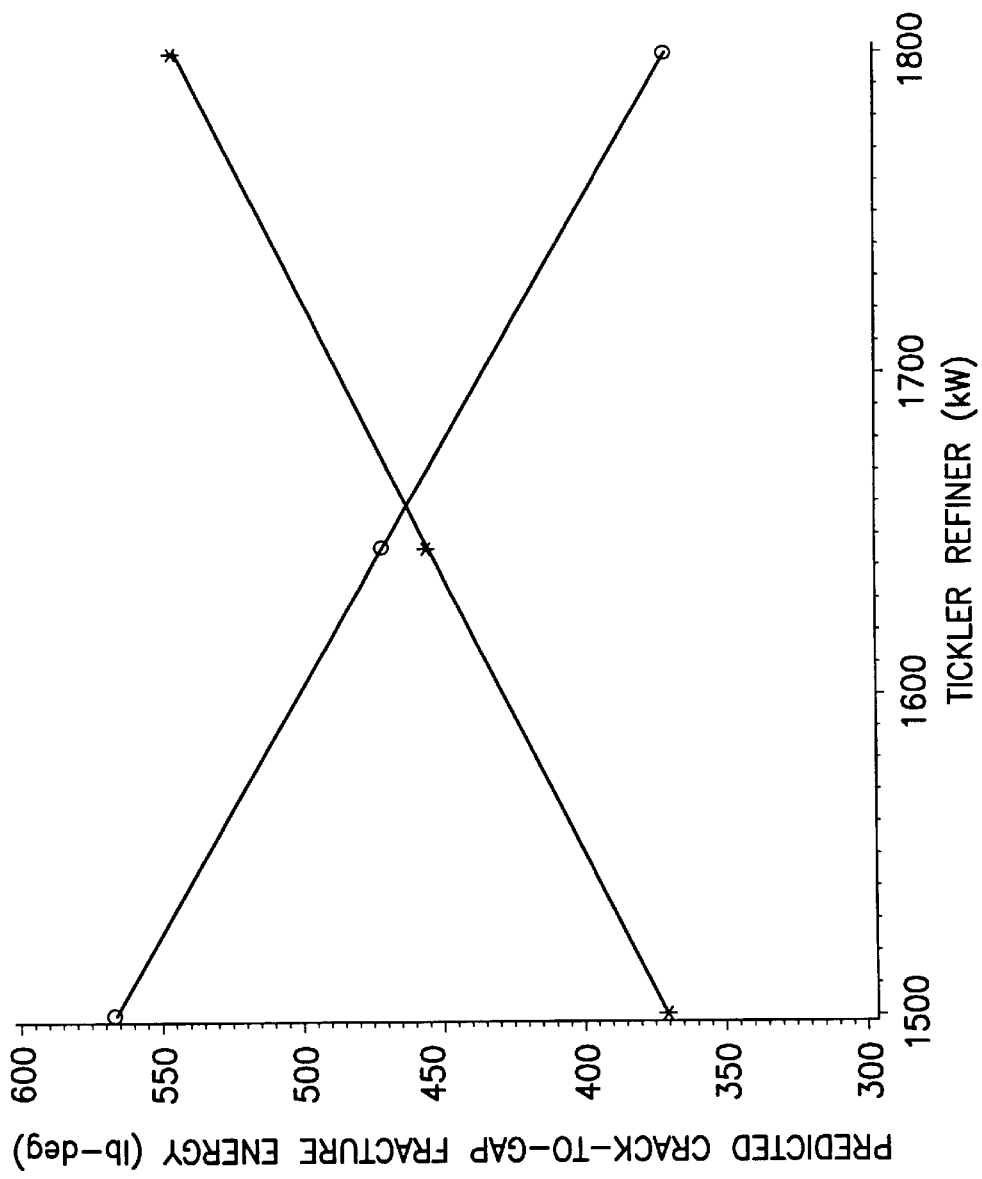
FIG. 10 is a graphical representation of how the predicted crack-to-gap fracture energy (lb*deg) varies with respect to tickler refining energy (kW) for two different top-ply coverages: (❈) 26 wt. %; (+) 36 wt. %.
Figure 11:
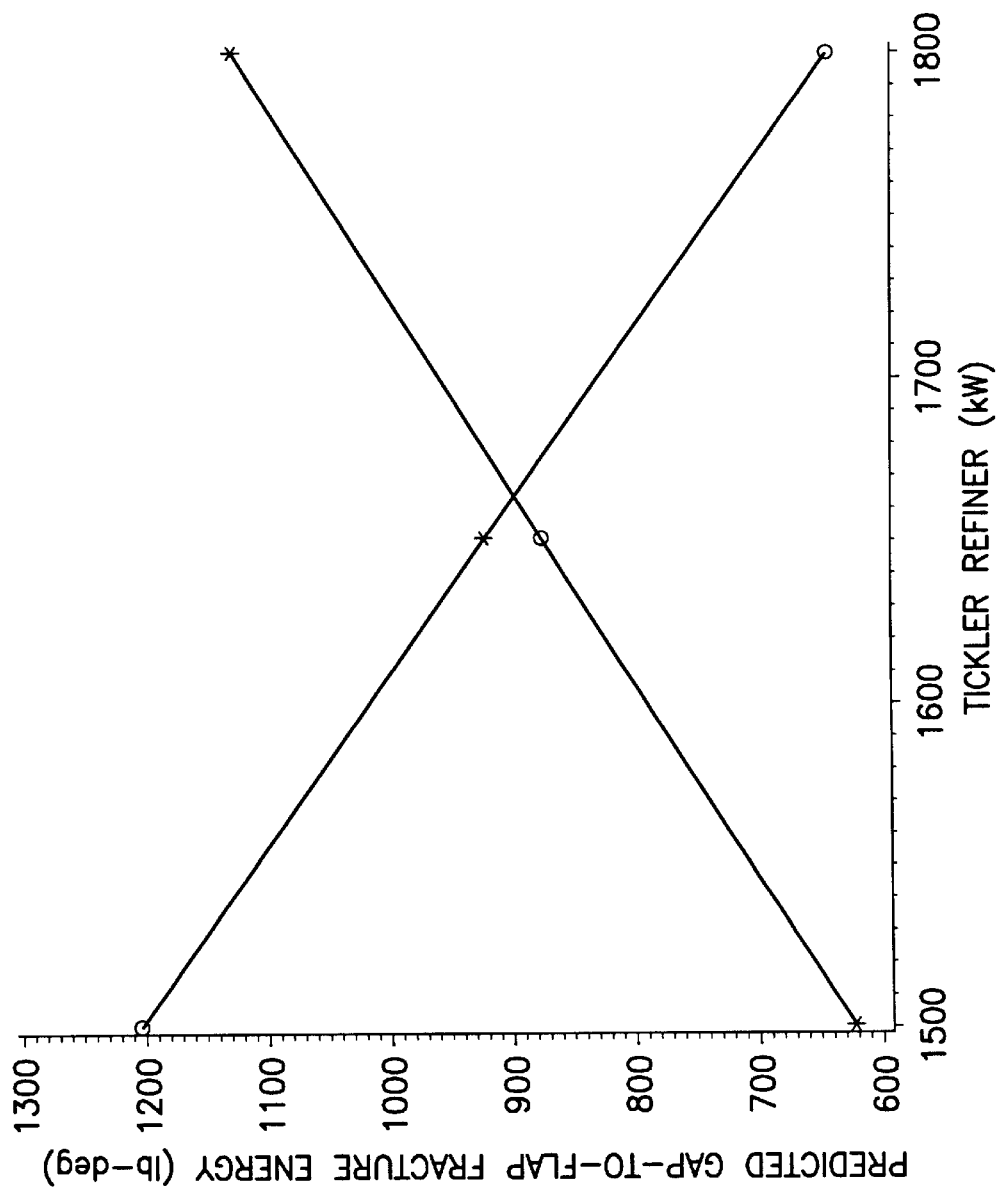
FIG. 11 is a graphical representation of how the predicted gap-to-flap fracture energy (lb*deg) varies with respect to tickler refining energy (kW) for two different top-ply coverages: (❈) 26 wt. %; (+) 36 wt. %.
Figure 12:
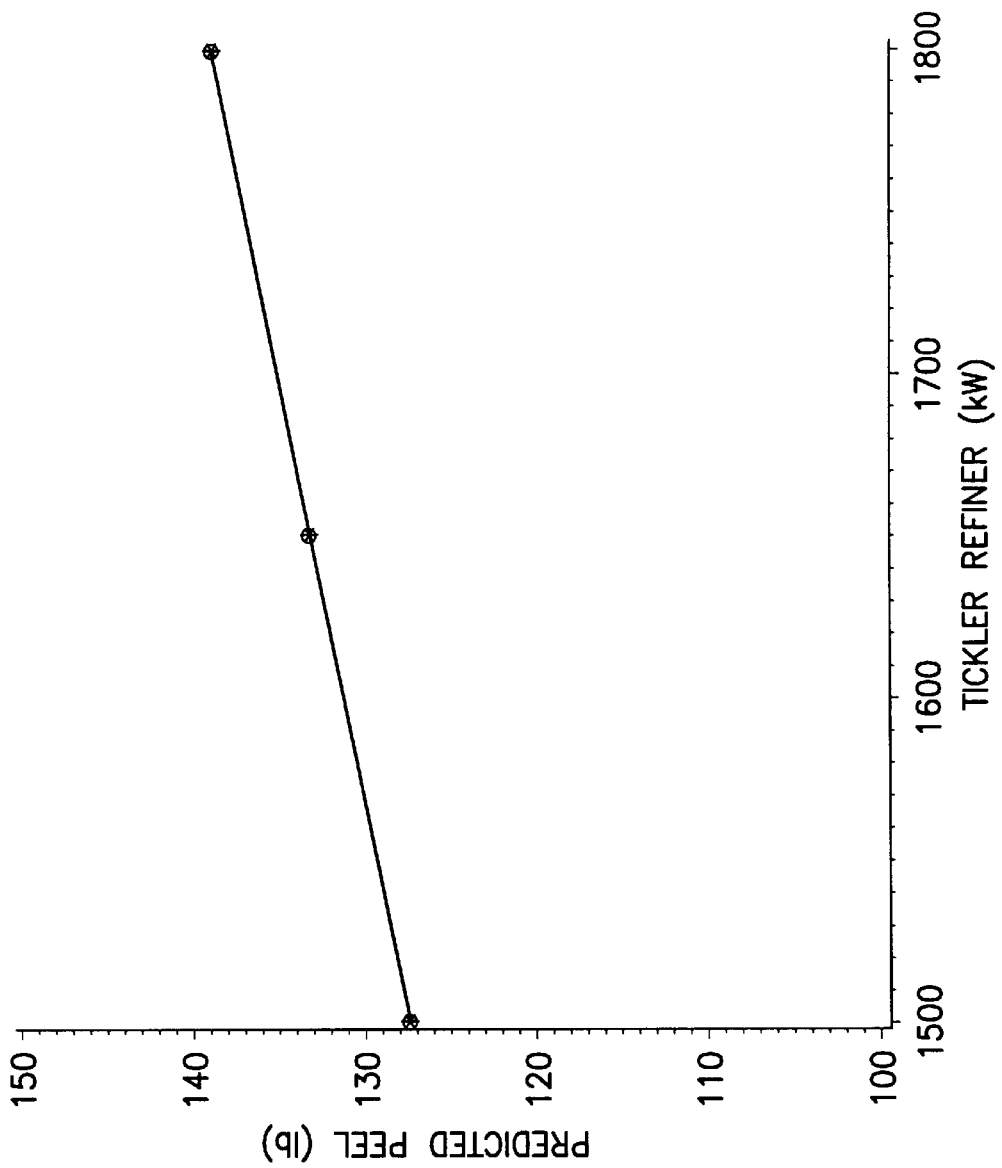
FIG. 12 is a graphical representation of how the predicted peel (or delamination) load (lb) varies with respect to tickler refining energy (kW) for two different top-ply coverages: (❈) 26 wt. %; (+) 36 wt. %. The primary refining energy was 1,300 kW; relative humidity was 50%.
Figure 13:
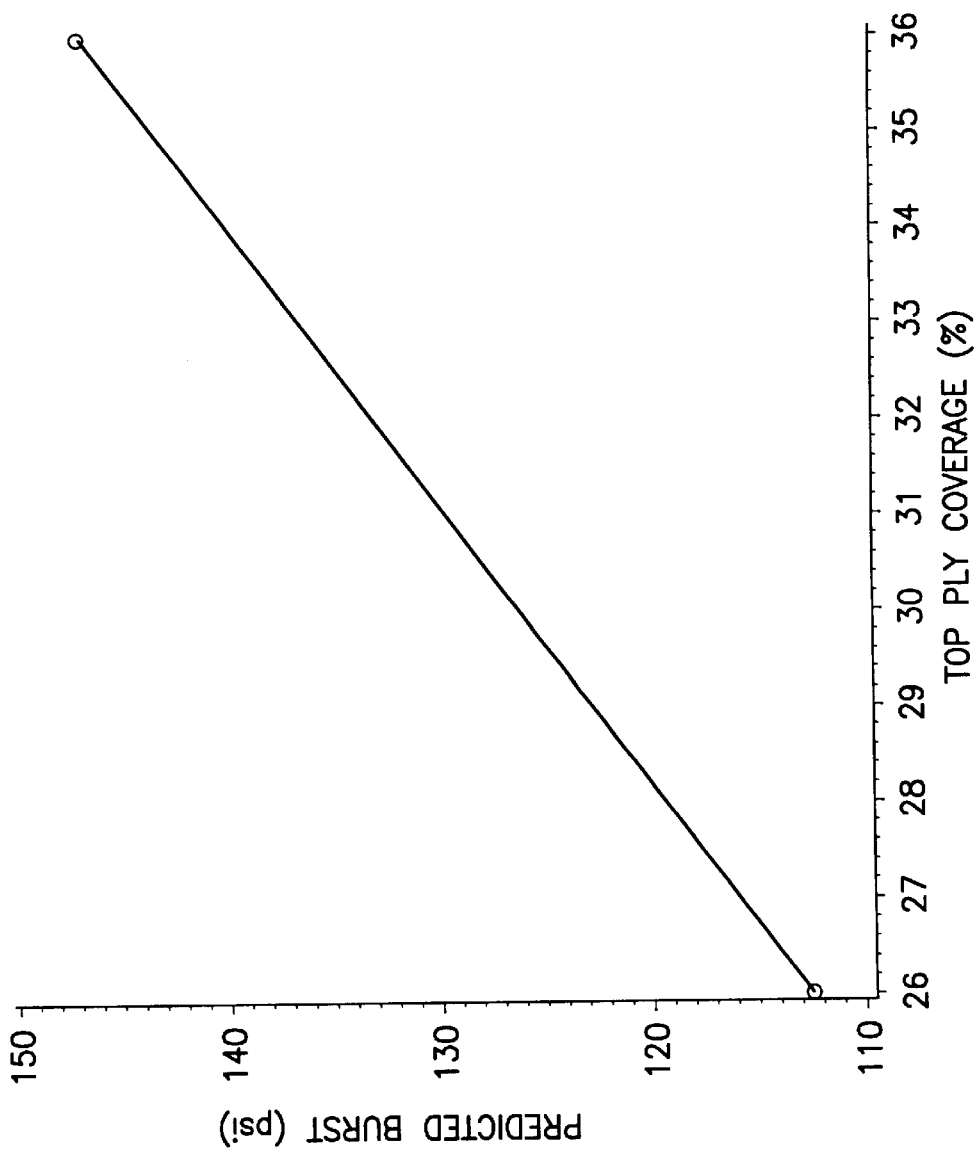
FIG. 13 is a graphical representation of how the predicted burst strength (lb) varies with respect to top-ply coverage (wt. %). The primary refining energy was 1,300 kW; relative humidity was 50%.

The top-ply fracture tester is depicted in FIGS. 2 and 3. To allow for the gradual material "degradation", i.e. cracking, within the outermost ply, the top-ply fracture tester mechanism is designed to bend any multi-ply film- or sheet-like structure, e.g. linerboard, around a ⅛-inch vertical (fixed) spindle 2 supported by a spindle support structure 4. In so doing, the sample S (see FIG. 2) will experience a net resultant tensile force. The sample (e.g., 1 inch wide and 5.75 inch long) is firmly held between two air (pneumatic) clamps 6 and 8. The opposing surfaces of the jaws of these air clamps have transverse grooves to ensure no slippage of the paperboard sample S during bending. Air is supplied to the clamps from a pressurized source via air lines 32 by operation of an air supply switch 35.

Air clamp 6 is fixedly coupled to a load cell 10 via a rod 12. The rod 12 is vertically supported by a mounting bracket 24 attached to the base 30. The load cell 10 is attached to an L-shaped bracket 26, the latter also being mounted to the base 30. The load cell 10 is thus coupled to the air clamp 6 via rod 12 and measures the sample load response during bending.

The other air clamp 8 is mounted to one end of a rod 16. The other end of rod 16 has a spring housing 18 mounted thereto. The rod 16 is slidably supported by a mounting bracket 22 attached to the base 30. Thus the assembly of the air clamp 8, the spring housing 18 and the rod 16 is axially slidable as a unit. A spring 14 is installed inside the spring housing 18 and couples the assembly to a fixed rod 17 that has a radial flange at one end. The spring 14 applies a tensile load to the sample. The rod 17 is fixedly supported by a mounting bracket 20. The rod 17 and a hole in the mounting bracket 20 are both threaded to allow adjustment of the axial position of the rod 17, which in turn allows the operator to adjust the tension applied by spring 14 depending on the basis weight of the material being tested.

Referring to FIG. 3, the brackets 20 and 22 are both mounted to a rotating or turning arm 28. The turning arm is rotatable about the axis of spindle 2, preferably to a maximum of about 160 degrees. As the turning arm swings, it carries the air clamp 8, causing the latter to rotate about the spindle axis, which in turn causes the sample S to bend around the spindle 2. In FIG. 3, the turning arm 28 is shown in the starting position A and in a rotated position B. As is best seen in FIG. 3, the spindle support structure 4 is mounted to the top of base 30. The turning arm 28 is rotatably mounted to base 30 by means of a bearing (not shown).

The turning arm 28 is rotated under the control of a computer 34, which is preferably incorporated in the test stand (as seen in FIG. 2). The computer 34 supplies the appropriate command to a motor controller (not shown) in response to depression of a "run" key on an operator interface 38. In response to the "run" command from the computer, the motor controller activates an electric motor (not shown). The electric motor has an output shaft (not shown) which is coupled to the turning arm 28 via a drive train (e.g., a gear assembly). The arm 28 can be set to rotate at varying speeds; for example, successful tests have been conducted with the arm rotational speed set at 1 degree/second. Testing requiring faster rates of elongation may be accommodated by varying the speed of the rotating arm.

As the turning arm 28 rotates, a position detector (not shown) detects the angular position of the arm and outputs an analog signal. This analog signal is converted to a digital signal representing arm angular position, which is sent to the computer 34. At the same time, the load cell 10 measures the tensile force or load being applied to the sample during rotation of the turning arm 28 and outputs an analog signal. This analog signal is converted to a digital signal representing tensile load, which is sent to the computer 34. Thus the computer simultaneously acquires tensile load data and angular position (i.e., displacement) data. The computer is programmed to generate a characteristic, real-time load-elongation curve (e.g., of the type shown in FIG. 1) for display on a display monitor 50.

As in tensile testing regimes and the like, the sample's strain rate is critical to the fundamental material properties being recorded. While the board's plastic component of deformation is, for instance, an inherent material property, and hence will be true in all (correct) testing conditions, values will vary for significantly different strain rates. For the preferred top-ply fracture tester design, the strain rate is affected by three factors: the spring load, the arm rotational speed and the gauge length [the distance between the two free edges of the clamps]. It is thus imperative that all measured values be quoted with corresponding rate of elongation, or arm speed. For the example where the sample width was 1 inch wide, sample length was 5.75 inch long, and the arm speed was 1 degree/second, the gauge length was fixed at 4 inches. When in operation, a characteristic, real-time load-elongation curve is obtained. The testing operation and relevant calculations are controlled via a computer program. The test results are displayed on the display monitor and can be output to a printer in response to a print command input via the operator interface.

Using the top-ply fracture tester, an operator is able to correlate material changes in a multi-ply board with "damage" phenomena occurring physically, which are, relatively speaking, easily detectable. When a two-ply linerboard sample is tested as described above, the operator would visually notice three distinct phenomena taking place at three discrete intervals: (1) the development of a (macro) crack as the sample is bent around the spindle; then (2) the opening up of the (macro)crack; and finally (3) the complete separation of the fibers, just prior to eventual failure and delamination of the top ply from the base ply. These crack, gap and flap stages represent the entire zone of plastic deformation while subjecting the top ply to a net tensile state of stress. Plastic deformation in linerboard is thus characterized by two components: the energy consumed during the crack-to-gap transition and that consumed during the gap-to-flap transition. Each component, or both, may be optimized to improve certain aspects of the board's ability to deform plastically, and, in turn, resistance to cracking. Such optimization involves the steps of: (a) selecting or choosing a value of a key operational parameter; (b) manufacturing linerboard using the selected value; (c) measuring the energy consumed during either or both of the crack-to-gap and gap-to-flap transitions for samples of the linerboard manufactured in step (b); (d) determining that the measured energy lies outside a desired range for achieving improved score-line cracking resistance; (e) adjusting the value of said key operational parameter; (f) manufacturing linerboard using the adjusted value; and (g) measuring the energy consumed during either or both of the crack-to-gap and gap-to-flap transitions for samples of the linerboard manufactured in step (f). Steps (d) through (g) are repeated until it is determined that the measured energy lies inside the desired range, in which case no further adjustments of the key operational parameter are necessary. Obviously, more than one key operational parameter can be adjusted during this process until linerboard having the desired material properties is produced.

The energy consumed during plastic deformation in the top ply of the linerboard samples is preferably measured using the equipment shown in FIGS. 2 and 3. The visual detection of the crack, gap and flap is recorded by pressing a respective pre-specified alphanumeric key on the user interface 38, e.g., a keypad, for each event. Once the test is complete, the computer program computes the (elastic and plastic) energies consumed from inception to failure of the single ply. Generally, the following is determined from a specimen's load-elongation curve: (1) energy consumed during elastic deformation (up to crack initiation); (2) energy consumed during crack-to-gap (the first plastic component); (3) energy consumed during gap-to-flap (second plastic component); and (4) energy consumed during crack-to-flap [(total plastic contribution, or sum of (2) and (3)] All of these values are computed along with the standard deviations, which may further help indicate two things: operator's precision (the larger the standard deviation, the worse is the operator's accuracy for recording crack, gap and flap) and sample variability (for instance, the standard deviation tends to be higher for recycle furnishes owing to inherent variability in pulp quality and, hence, mechanical properties of the board). Crack propagation is observed in real-time in the top ply, and as material degradation continues, in the base ply (or succeeding plies, as the case may be).

The purpose of the designed experiments was to examine the influence of the following variables on the propensity for score-line cracking in white-top linerboard: top- and base-ply refining, filler content, starch content (in both plies), top-ply coverage (i.e., the weight of the top ply), wet press load, virgin vs. recycled fiber contents in the top ply, and (virgin) softwood vs. hardwood content in the top ply. The influence of top-ply coverage, refining, starch and filler contents, and softwood content were found to exhibit the most pronounced effect (when compared to the other variables) on the ability of the board to absorb energy prior to failure, and consequently its propensity for cracking.

The first designed experiment (DOE1) comprised a three-variable, full-factorial design with two additional conditions (Runs 11 and 12 in Table 1) to investigate the effects of maximizing the starch shower, and another for minimizing refining energy. The three variables were: top-ply coverage, top-ply tickler refining energy and top-ply wet-end starch. The furnish for the top ply was 100% recycled fibers. The base sheet was maintained, during the entire trial, at the following conditions: primary refining=1524±7 kW, tickler refining=1592±72 kW, virgin refining=373±6 kW, alkenyl succinic anhydride (ASA)=2.90 lb/ton, ASA starch=3.00 lb/ton, wet-end starch 18.00 lb/ton, alum=16.5 lb/ton. The values (actual centerline values) of the three variables for different runs are set forth in Table 1.

TABLE 1

| Run | Top-Ply Coverage (%) | Tickler Refining (kW) | Wet-End Starch (lb/ton) | Starch Shower (lb/kg-ft$^2$) |
|---|---|---|---|---|
| 1 | 36 | 1452 | 19 | 0.05 |
| 2 | 38 | 1746 | 30 | 0.05 |
| 3 | 38 | 1647 | 26 | 0.05 |
| 4 | 37 | 1600 | 24.5 | 0.05 |
| 5 | 36 | 1452 | 30 | 0.05 |
| 6 | 38 | 1451 | 30 | 0.05 |
| 7 | 37 | 1599 | 25 | 0.05 |
| 8 | 36 | 1748 | 19 | 0.05 |
| 9 | 36 | 1754 | 30 | 0.05 |
| 10 | 38 | 1748 | 19 | 0.05 |
| 11 | 36.7 | 1604 | 25 | 0.269 |
| 12 | 36 | 800 | 19 | 0.054 |

The experimental results for fracture energy are given Table 2, wherein the second column gives the energy consumed up to crack initiation; the third column gives the energy consumed during the crack-to-gap transition, the fourth column gives the energy consumed during the gap-to-flap transition; and the fifth column gives the sum of the energies consumed during the crack-to-gap and the gap-to-flap transitions. For all specimens tested, crack propagation was in the cross direction (as in most scoring scenarios).

TABLE 2

| Run | To Crack (lb*deg) | Crack-to-Gap (lb*deg) | Gap-to-Flap (lb*deg) | Crack-to-Flap (lb*deg) |
|---|---|---|---|---|
| 1 | 1807 | 379 | 338 | 717 |
| 2 | 2002 | 278 | 362 | 639 |
| 3 | 1881 | 369 | 396 | 765 |
| 4 | 1528 | 363 | 568 | 932 |
| 5 | 1621 | 393 | 659 | 1051 |
| 6 | 1744 | 420 | 676 | 1096 |
| 7 | 1613 | 429 | 695 | 1124 |
| 8 | 1713 | 571 | 536 | 1107 |
| 9 | 1580 | 570 | 670 | 1239 |
| 10 | 1638 | 503 | 574 | 1078 |
| 11 | 1591 | 455 | 760 | 1215 |
| 12 | 1402 | 385 | 814 | 1199 |

The experimental results for other material properties are given in Table 3. All samples were allowed to condition for about 30 minutes in 50±5% relative humidity and 23±1° C. before testing in the same controlled environment.

TABLE 3

| Run | Peel (lb) | Burst (psi) | CD Ring Crush (lb) |
|---|---|---|---|
| 1 | 116 | 85 | 78 |
| 2 | 126 | 87 | 76 |
| 3 | 151 | 86 | 80 |
| 4 | 129 | 85 | 83 |
| 5 | 145 | 84 | 78 |
| 6 | 130 | 87 | 79 |
| 7 | 138 | 89 | 80 |
| 8 | 117 | 86 | 78 |
| 9 | 153 | 86 | 78 |

TABLE 3-continued

| Run | Peel (lb) | Burst (psi) | CD Ring Crush (lb) |
|---|---|---|---|
| 10 | 133 | 87 | 77 |
| 11 | 161 | 91 | 78 |
| 12 | 124 | 87 | 76 |

Below the outline of the outcome of the statistical analysis of the responses as a function of the variables.

Variables:

$x1$ = (top-ply coverage − 37)

$x2$ = (top-ply tickler refining − 619.7)

$x3$ = (top-ply wet-end starch − 25.25)

$x12$ = represent the interaction between $x1$ and $x2$ (similarly for $x13$ and $x23$)

Covariates:
  $z1$ = (relative humidity − 48.8)
Responses:

$A$ = energy consumed during crack-to-gap $B$ = energy consumed during gap-to-flap $C$ = energy consumed during crack-to-flap

= $A + B$ $D$ = energy consumed up to during crack initiation $E$ = peel $F$ = CD ring crush The factors x1, x2, etc. are actually centered variables. They are mathematically equal to the variable named minus its average value over the trial. Thus, for instance, the interaction term x12 would represent:

$x12$ = (top-ply coverage − $a$) ∗ (tickler refining − $b$)

= $ab - b$ ∗ [top-ply coverage] − $a$ ∗ [tickler refining] +

[top-ply coverage] ∗ [tickler refining]

where a and b are the average values for top-ply coverage and tickler refining, respectively. Table 4 illustrates the important factors in predicting each response.

TABLE 4

| Response | x1 | x2 | x3 | X12 | x13 | x23 | z1 | $R^2$ | F-Test |
|---|---|---|---|---|---|---|---|---|---|
| A | Yes | | | Yes | Yes | | Yes | 0.86 | 14 |
| B | | | | Yes | Yes | | | 0.52 | 6 |
| C | | | | Yes | Yes | | | 0.65 | 9 |
| D | | | | | Yes | | | 0.27 | 4 |
| E | | Yes | | Yes | | | | 0.65 | 9 |
| F | | Yes | Yes | | | Yes | | 0.6 | 4 |

In Table 4, useful predictive (linear) models are indicated for A, B, C and E. A model, for example, representing the energy consumed during the crack-to-gap transition, A, actually contains effects of all three variables in the designed experiment and an effect of relative humidity. Supporting graphs for statistical analysis can be found in FIGS. 4-9; the predictive equations were determined as follows.

$A = 440.053188 - 39.914418*X1 - 0.415916*X12 - 6.881632*X13 - 121.183515*Z1$ $B = 572.144361 - 0.644241*X12 - 18.230696*X13$ $C = 1014.025388 - 1.110104*X12 - 26.396360*X13$ $D = 1699.695716 + 18.577548*X13$ $E = 135.006064 + 1.244657*X3 - 1.722948*X13$ $F = 78.295351 + 0.016720*X2 - 0.741877*X3 - 0.004623*X23 + 14.105579*Z1$

Even though the ranges examined for the variables were not broad enough to discern definitive (overall) values for cracking-resistance performance, phenomenological trends were clearly indicated based on the above analysis, viz.:

(1) Top-ply coverage seemed to be the principal (individual) factor exhibiting important effects with respect to energy consumption beyond cracking. However, the interactions between the factors had a strong presence. A more likely reason for the difficulty in ascertaining the effects of (other) individual factors was the low ranges (see centerline values above) permitted on the papermachine. (Refer to FIGS. 4-7.)

(2) At the lower refining level (1450 kW), the predicted energy consumed during the crack-to-gap transition did not change with increasing top-ply coverage for higher starch levels (30 lb/ton). When the refining level was increased (1750 kW), the predicted energy sharply decreased with increasing top-ply coverage for the same (high) starch level. At a lower starch level (20 lb/ton), the situation was dramatically different: The rate of decline in predicted crack-to-gap energy with increasing top-ply coverage was more subdued at a high refining level (1750 kW); whereas for a lower refining level (1450 kW), the predicted energies increased with increasing coverage at a low starch level (20 lb/ton). (Refer to FIG. 4.)

(3) A similar trend occurred with the energy consumed during the gap-to-flap transition for low refining levels (1450 kW). At a higher refining level (1750 kW), the predicted gap-to-flap energy decreased sharply with increasing coverage for a high starch level (30 lb/ton)—as in the case for the crack-to-gap transition. However, the predicted gap-to-flap energy was almost unchanged with increasing coverage for a low starch level (20 lb/ton). A non-changing or decreasing gap-to-flap energy would indicate a decline of the board's ability to plastically deform, i.e., both starch levels are detrimental. The starch levels need to be reduced to capture the effects of top-ply coverage at higher refining levels. (Refer to FIG. 5.)

(4) The predicted peel load (i.e., the load required to separate plies) behaved in a different manner to the above. At a low refining level (1450 kW), peel load increased with top-ply coverage for low starch levels (20 lb/ton). The converse was true for a high starch level (30 lb/ton). At a higher refining level (1740 kW), the trends for high and low starch were almost identical. (Refer to FIGS. 8 and 9.)

(5) Run 11 was carried out to learn about the effect of the starch shower (on the center point). It was difficult to discern from this sole run any overwhelming pattern related to the energy consumption during or after cracking. However, it was evident that peel strength increased substantially, and our comparative analysis (above) indicated that higher peel loads affect resistance to cracking detrimentally. (Refer to the relevant variable and value in Tables 2 and 3 presented above.)

(6) Substantially lowering tickler refining (Run 12) indicated that resistance to cracking (principally crack-to-gap and gap-to-flap energies) improved when compared with the center point. There was a concomitant decrease in peel load when refining was reduced to 800 kW. (Refer to results set forth above.)

The changes in refining energy levels did not impact freeness to the expected levels. Based on the data, the median freeness seemed proportional to increasing refining levels; however, large variations in freeness existed at any one particular refining energy level. This could have been due to one or both of the following: (i) the existing refining plates were not inducing "proper" fiber development; (ii) the small range of refining energy levels precluded a significant impact on the freeness levels.

A mini designed experiment (DOE2) was carried out on 42-lb white-top linerboard to examine the effect of two variables: 2nd press load and the uni-run draw. Limited ranges of centerline values for the variables were used. In spite of the limited ranges, the analysis showed a trend of slack draws and higher (second) press loads being more conducive to better cracking resistance. It is also indicated that the results were appreciably confounded: The two variables play a role not as significant as top-ply coverage, refining energy levels and starch content.

Thus, experimentation with the 42-lb white-top linerboard clearly indicated that there were three principal factors influencing the board's propensity for score-line cracking. They are: top-ply coverage, refining energy level and starch content. A further experiment (DOE3) was conducted in an effort to test the validity, and subsequently the optimal ranges, of these factors insofar as the resistance to cracking of 69-lb white-top linerboard was concerned.

DOE3 was a two-variable factorial experiment, with top-ply coverage and tickler refining energy level as the two variables. As it happened, the primary refining level was allowed to vary (in order to meet the specifications for the extreme cases); it was thus considered as a covariate in the statistical analysis of (some of) the data. The furnish comprised 70% virgin softwood and 30% virgin hardwood in the top ply. The base was roughly 95% OCC (old corrugated containers) and the remainder was virgin pulp. The centerline data are set forth in Table 5.

TABLE 5

| Run | Top-Ply Coverage (%) | Tickler Refining (kW) | Primary Refining (kW) | Wet-End Starch (lb/ton) | Starch Shower |
|---|---|---|---|---|---|
| 1 | 26.4 | 1543 | 1800 | 3 | Off |
| 2 | 26.2 | 1802 | 1800 | 3 | Off |
| 3 | 32.2 | 1614 | 1311 | 3 | Off |
| 4 | 35.9 | 1795 | 1301 | 3 | Off |
| 5 | 35.7 | 1556 | 1297 | 3 | Off |

No starch was applied at the size press. The top ply had approximately 3 lb/ton of ASA and 9.96 lb/ton of ASA starch. No alum was used in the top ply, and only traces of PCC (precipitate calcium carbonate) were present in the wet end. The base had the following additives: Nugen (retention aid)=1.7 lb/ton, ASA=1.51 lb/ton, ASA starch=3 lb/ton, wet-end starch=10 lb/ton, alum =10 lb/ton. The primary refiner was maintained at about 1030 kW and the tickler at 1380 kW (and 360 kW for refining the virgin portion of the base ply).

The results for DOE3 are set forth in Tables 6 and 7.

TABLE 6

| Run | To Crack (lb*deg) | Crack-to-Gap (lb*deg) | Gap-to-Flap (lb*deg) | Crack-to-Flap (lb*deg) |
|---|---|---|---|---|
| 1 | 2142 | 484 | 1183 | 1667 |
| 2 | 1815 | 360 | 575 | 935 |
| 3 | 1717 | 350 | 641 | 991 |
| 4 | 1959 | 627 | 1124 | 1751 |
| 5 | 1822 | 498 | 957 | 1455 |

TABLE 7

| Run | Peel (lb) | Burst (psi) | CD Ring Crush (lb) |
|---|---|---|---|
| 1 | 150 | 147 | 150 |
| 2 | 132 | 136 | 147 |
| 3 | 130 | 134 | 151 |
| 4 | 139 | 146 | 145 |
| 5 | 130 | 147 | 145 |

The relevant predictive equations and correlation matrix obtained from the statistical analysis are as follows:

Variables:

$x1$=(top-ply coverage−31.28)

$x2$=(top-ply tickler refining−1662)

Correlates:

$z1$=(relative humidity−54.6)

$z2$=(primary refining−1501.8)

The responses were the same as for DOE1.

Predictive Equations:

$$A = 464.495994 + 0.121253 * X12$$

$$B = 898.061051 + 0.359068 * X12$$

$$C = 1362.557045 + 0.480321 * X12$$

$$D = 1891.000000 + 13.153650 * Z1$$

$$E = 136.200000 + 0.039216 * X2 + 1.175477 * Z1 - 0.014476 * Z2$$

$$F = 142.000000 + 3.474055 * X1 + 0.430040 * Z1 + 0.045653 * Z2$$

The correlation matrix for centered design variables and centered covariates (coefficients×100 and rounded) appears in Table 8.

TABLE 8

|  | X1 | X2 | X12 | X11 | Z1 | Z2 |
|---|---|---|---|---|---|---|
| X1 | 100 | 0 | 12 | −32 | −56 | −96 |
| X2 | 0 | 100 | −12 | 28 | −52 | 8 |
| X12 | 12 | −12 | 100 | 0 | 56 | −8 |
| X11 | −32 | 28 | 0 | 100 | 36 | 60 |
| Z1 | −56 | −52 | 56 | 36 | 100 | 64 |
| Z2 | −96 | 8 | −8 | 60 | 64 | 100 |

It should be noted that the models were weakened by a change in primary refining made by the operators at the beginning of the experiment. A high correlation thus resulted between primary refining and top-ply weight, whereupon the former could not be used as a covariate in the regression analysis to examine, for instance, the effects of tickler refining or its interaction on top-ply weight (which are known to be causal factors).

FIGS. 10–13 reveal the outcome of the statistical analysis. One can ascertain from a careful examination of the results that higher top-ply coverage, in the range 33–36%, definitively improves cracking resistance. Optimal resistance may, however, be achieved at primary refining energy levels lower than 1400 kW and at tickler refining energy levels lower than 1200 kW. Lowering the refining energy further is even more beneficial to improving cracking resistance, as long as there is proper fiber development. As evinced by the results, lowering starch content in the ply further contributes to improving the crack resistance, since the sheet's ability to plastically deform improves appreciably.

Moreover, in addition to all that has been stated above, a mill should assess the quality of the virgin pulp to be utilized. Aspects related to the pulp viscosity, percent fines, mean fiber length, etc. play an important role in (further) improving, or worsening, the sheet's plasticity, and subsequently impacting its propensity for score-line cracking. An analysis of different pulps revealed that the viscosity varies remarkably. Pulp suspensions of varying viscosity can introduce variations from Newtonian behavior, as in the occurrence of shear thinning and shear thickening. As such, this will contribute to changes in the internal state of stress of the final product and its ability to absorb energy; consequently affecting the resistance to cracking. Therefore, a pulp quality verification and control protocol should be enforced by the mill for their entire production to ensure favorable results. The inventors performed screening tests using different pulps in order to ascertain the effect of pulp viscosity on the crack-to-gap and gap-to-flap energies. It was determined from these screening tests that the pulp viscosity should ideally be around 20 cps.

The final product should have the following material properties to ensure satisfactory score-line cracking resistance: (1) energy consumed up to crack initiation >1400 lb*deg; (2) energy consumed during the crack-to-gap transition >650 lb*deg; and (3) energy consumed during the gap-to-flap transition >1700 lb*deg. These properties can be measured using the top-ply fracture tester disclosed herein. This tester provides an accurate measure of the energy consumed by the top ply during plastic deformation prior to failure. The two-component plastic energy, crack-to-gap and gap-to-flap, provide excellent correlations with field performance.

Equipped with a predictive measure, three machine trials (described above) were carried out to validate the factors that influence score-line cracking resistance the most. Principally, the aim was to produce a two-ply board whereby the top ply was designed to plastically deform, without the need to incur extensive deformation in the base ply. The inter-ply bonding must allow the top ply to "slide" over the base, but without causing delamination of the two plies. This was shown to have been achieved by substantially lowering the wet-end starch in both the top and base plies, reducing filler content, reducing refining energy levels and increasing top-ply coverage. The results of the conversion of the entire production at a container plant was proven to be successful: No score-line cracking was observed in converting 69-lb white-top linerboard used to produce single-wall structures for the most severe applications, such as watermelon boxes, cantaloupe boxes and Calpine ends.

In accordance with the preferred embodiment of the invention, the top-ply fracture tester was utilized as the cornerstone behind improving the functionality (score-line cracking resistance) of a two-ply linerboard. The test data showed a clear trend how the propensity for cracking (as quantified by the percent field cracking, which is the crack length percent relative to the length of the score line) correlates with the energy consumed during the crack-to-flap transition, or the total energy consumed during plastic deformation. The following factors were found to affect the top ply's ability to plastically deform: the furnish type (virgin versus recycle), furnish quality (e.g. pulp viscosity), degree of fiber development (refining), inter-ply bonding, top-ply coverage, and starch and filler content. The interacting effects between each, or several of the above factors, result in the development of larger plastic zones of deformation in the top ply.

Over time, key operational parameter data for various manufactured grades of multi-ply linerboard can be accumulated in a databank. The key operational parameter data in the databank would comprise top-ply coverage, top-ply fiber furnish composition (virgin vs. recycled fibers), refining energy of the top-ply furnish, starch and filler contents in the top ply, and top-ply pulp viscosity. In accordance with another preferred embodiment of the invention, multi-ply linerboard can be manufactured by a method comprising the following steps: manufacturing different grades of multi-ply paperboard using key operational parameters; measuring the energy consumed during plastic deformation of the top ply of test samples of paperboard taken from multiple production runs; for each of a multiplicity of production runs, storing energy consumption measurements and associated key operational parameters in a databank; retrieving from said databank a set of key operational parameter data for a grade of paperboard; and manufacturing a grade of paperboard product using the key operational parameters retrieved from said databank.

In conclusion, the top-ply fracture tester disclosed herein measures fundamental properties that show reproducible, accurate correlation with field performance. Using the top-ply fracture tester, one is able to develop tools that enable the prediction of cracking propensity in terms of inherent material parameters (energy consumption during plastic deformation, or crack-to-flap) and papermaking conditions (that ultimately affect the board's material properties). By balancing the magnitudes of the two plastic components (crack-to-gap and gap-to-flap), one will also be better able to understand the limits to which the papermaking conditions and structural parameters (e.g., top-ply coverage) could be changed if the basic fiber properties (e.g., pulp furnish and/or quality) change, so as to produce optimal cracking-resistant linerboard.

It should also be noted that capabilities to predict score-line cracking propensity must intrinsically be associated with measuring energy absorption in the subject material, specifically, the energy consumed during plastic deformation. Routine mechanical measures (such as tensile strength, TEA, etc.) have been shown not to correlate, as expected from a theoretical standpoint.

While the invention has been described with reference to preferred embodiments, it will be understood by those skilled in the art that various changes may be made and equivalents may be substituted for elements thereof without departing from the scope of the invention. For example, the variables in the predictive equations may optionally include pulp viscosity. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

What is claimed is:

1. A method for making multi-ply paperboard, comprising the following steps:
   (a) formulating a mathematical model of energy consumed during plastic deformation of a top ply of a multi-ply paperboard as a function of a plurality of variables, each variable representing a papermaking condition, a structural parameter or a pulp property;
   (b) determining a desired value or range of values for the energy consumed during plastic deformation;
   (c) determining respective values for each of said plurality of variables which, when inserted in said mathematical model, result in an energy consumption during plastic deformation of said top ply substantially equal to said desired value or lying within said desired range; and
   (d) manufacturing a multi-ply paperboard in accordance with said determined respective values.

2. The method as recited in claim 1, wherein one of said variables is top-ply coverage.

3. The method as recited in claim 1, wherein one of said variables is top-ply furnish refining energy.

4. The method as recited in claim 1, wherein one of said variables is top-ply pulp viscosity.

5. The method as recited in claim 1, wherein one of said variables is top-ply starch content.

6. A method for manufacturing multi-ply paperboard, comprising the following steps:
   (a) manufacturing a multi-ply paperboard of a particular grade using a first set of respective values for a plurality of key operational parameters that affect energy consumed during plastic deformation of a top ply of said multi-ply paperboard;
   (b) measuring the energy consumed during plastic deformation of said top ply;
   (c) determining that the measured energy consumption is different than a desired energy consumption;
   (d) determining a second set of respective values for said plurality of key operational parameters that will produce an energy consumed during top-ply plastic deformation closer to said desired energy consumption than was said measured energy consumption; and
   (e) manufacturing multi-ply paperboard of said particular grade having respective values for said plurality of key operational parameters that are respectively substantially equal to said second set of respective values.

7. The method as recited in claim 6, wherein one of said key operational parameters is top-ply coverage.

8. The method as recited in claim 6, wherein one of said key operational parameters is top-ply furnish refining energy.

9. The method as recited in claim 6, wherein one of said key operational parameters is top-ply pulp viscosity.

10. The method as recited in claim 6, wherein one of said key operational parameters is top-ply starch content.

11. A method for manufacturing multi-ply paperboard comprising the steps of:
    (a) selecting a value of a key operational parameter;
    (b) manufacturing multi-ply paperboard using the selected value;
    (c) measuring the energy consumed during either or both of the crack-to-gap and gap-to-flap transitions for samples of the paperboard manufactured in step (b);
    (d) determining that the measured energy lies outside a desired range for achieving improved score-line cracking resistance;
    (e) adjusting the value of said key operational parameter;
    (f) manufacturing paperboard using the adjusted value; and
    (g) measuring the energy consumed during either or both of the crack-to-gap and gap-to-flap transitions for samples of the paperboard manufactured in step (f).

12. The method as recited in claim 11, wherein steps (d) through (g) are repeated until it is determined that the measured energy lies inside the desired range.

13. The method as recited in claim 11, wherein steps (d) through (g) are repeated until the measured energy consumed during the crack-to-gap transition is greater than 650 lb*deg.

14. The method as recited in claim 11, wherein steps (d) through (g) are repeated until the measured energy consumed during the gap-to-flap transition is greater than 1700 lb*deg.

15. A method for making multi-ply paperboard, comprising the following steps:
    (a) formulating a mathematical model of energy consumed during plastic deformation of a top ply of a multi-ply paperboard as a function of a plurality of key operational parameters;
    (b) determining a desired range of values for the energy consumed during plastic deformation of the top ply;
    (c) manufacturing a multi-ply paperboard in accordance with respective values for said plurality of key operational parameters;
    (d) measuring the energy consumed during plastic deformation of the top ply for samples of the paperboard manufactured in step (c);
    (e) determining that the measured energy consumed lies outside the desired range for achieving improved score-line cracking resistance;
    (f) adjusting the value of at least two of said operational parameters as a function of said mathematical model;
    (g) manufacturing a multi-ply paperboard using the adjusted values; and
    (h) measuring the energy consumed during plastic deformation of the top ply for samples of the paperboard manufactured in step (g).

16. A method for operating a paper mill, comprising the following steps:
    manufacturing different grades of multi-ply paperboard using key operational parameters;
    measuring the energy consumed during plastic deformation of the top ply of test samples of paperboard taken from multiple production runs;
    for each of a multiplicity of production runs, storing energy consumption measurements and associated key operational parameters in a databank;
    retrieving from said databank a set of key operational parameter data for a grade of paperboard; and
    manufacturing a grade of paperboard product using the key operational parameters retrieved from said databank.

17. The method as recited in claim 16, wherein one of said key operational parameters is top-ply coverage.

18. The method as recited in claim 16, wherein one of said key operational parameters is top-ply furnish refining energy.

19. The method as recited in claim 16, wherein one of said key operational parameters is top-ply pulp viscosity.

20. The method as recited in claim 16, wherein one of said key operational parameters is top-ply starch content.

21. A method for manufacturing a grade of multi-ply paperboard, comprising the following steps:

performing a factorial experiment to investigate the effects of key operational parameters on energy consumed during plastic deformation of a top ply of a multi-ply paperboard;

analyzing data acquired by said factorial experiment to derive a statistically significant mathematical model for energy consumed during plastic deformation of the top ply as a function of a plurality of key operational parameters;

selecting values for key operational parameters as a function of said mathematical model; and manufacturing paper using said selected values for said key operational parameters.

* * * * *